US00PP22538P2

(12) United States Plant Patent
Stever et al.

(10) Patent No.: US PP22,538 P2
(45) Date of Patent: Feb. 28, 2012

(54) ***PENNISETUM* PLANT NAMED 'CHERRY SPARKLER'**

(50) Latin Name: *Pennisetum setaceum*
Varietal Denomination: Cherry Sparkler

(75) Inventors: Karen R. Stever, Gainsville, GA (US); Ronald Strasko, Leola, PA (US)

(73) Assignee: Itsaul Plants LLC, Alpharetta, GA (US), 50% of Rights ( * ) Notice: Subject to any disclaimer, the term of this patent is extended or adjusted under 35 U.S.C. 154(b) by 0 days.

(21) Appl. No.: 12/927,708

(22) Filed: Nov. 22, 2010

(51) Int. Cl.
*A01H 5/00* (2006.01)

(52) U.S. Cl. ..... Plt./384

(58) Field of Classification Search ..... Plt./384
See application file for complete search history.

*Primary Examiner* — Annette Para
(74) *Attorney, Agent, or Firm* — Penny J. Aguirre

(57) ABSTRACT

A new cultivar of *Pennisetum setaceum* named 'Cherry Sparkler', characterized by its variegated foliage with distinct longitudinal stripes that are creamy white and green in color and flushed with pink when exposed to full sun with greater expression of the pink flush when growing in cooler temperatures, its height of 91 to 102 cm, and its blooms that open burgundy in color.

2 Drawing Sheets

Botanical classification: *Pennisetum setaceum.*
Varietal denomination: 'Cherry Sparkler'.

CROSS REFERENCE TO A RELATED APPLICATION

This application is related the a U.S. Plant Patent for the parent plant, *Pennisetum* Plant Named 'Fireworks' (U.S. Plant Pat. No. 18,504) and co-pending with a U.S. Plant Patent Application filed for a plant derived from the same parent plant that is entitled *Pennisetum* Plant Named 'Sky Rocket' (U.S. Plant Pat. No. 21,497).

BACKGROUND OF THE INVENTION

The present invention relates to a new and distinct cultivar of *Pennisetum setaceum* and will be referred to hereafter by its cultivar name, 'Cherry Sparkler'. 'Cherry Sparkler' represents a new cultivar of purple fountain grass; a warm-season, ornamental grass grown for container and landscape use.

The Inventors discovered and selected the new cultivar, 'Cherry Sparkler', as a culm sport of *Pennisetum setaceum* 'Fireworks' (U.S. Plant Pat. No. 18,504) during division of a stock plant of 'Fireworks' in a nursery in Alpharetta, Ga. in April of 2008.

Asexual reproduction of the new cultivar was first accomplished by culm division in Alpharetta, Ga. in May of 2008 by one of the Inventors. Asexual propagation by culm division has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Cherry Sparkler' from all other selections of *Pennisetum* known to the Inventors.

1. 'Cherry Sparkler' exhibits variegated foliage with distinct longitudinal stripes that are creamy white and green in color (most typically with green centers and creamy white margins) with the foliage becoming flushed with pink when exposed to full sun.
2. The pink flush of the foliage of 'Cherry Sparkler' begins on the margin of the leaf blades and spreads over the entire leaf with exposure to full sun with the pink flush more highly expressed when temperatures are cooler.
3. 'Cherry Sparkler' blooms heavily from May until frost in Georgia with plumes that open burgundy in color and turn light brown as they mature.
4. 'Cherry Sparkler' reaches a height of 91 to 102 cm (36 to 40 inches).

'Cherry Sparkler' can be most closely compared to the parent plant, 'Fireworks', which differs in having foliage that is variegated with longitudinal stripes of white, green and burgundy and in having a slightly taller plant height. 'Cherry Sparkler' can be most closely compared to the cultivars 'Rubrum' (not patented) and 'Sky Rocket'. 'Rubrum' differs from 'Cherry Sparkler' in having foliage that is non-variegated and burgundy in color when grown in full sun and green in color when grown in full shade and in having foliage that is broader in width (less fine). 'Sky Rocket' differs from 'Cherry Sparkler' in having foliage that is variegated with green and clearer white and lacks the pink flush that is observed on the foliage of 'Cherry Sparkler'. 'Sky Rocket' also differs from 'Cherry Sparkler' in being slightly taller in height and in having leaves that are broader in width (less fine).

BRIEF DESCRIPTION OF THE DRAWING

The accompanying colored photographs illustrate the overall appearance and distinct characteristics of plants the new *Pennisetum* and comparison plants as grown outside and in containers in Alpharetta, Ga.

The photograph in FIG. 1 was taken in October and illustrates the foliage coloration of 'Cherry Sparkler' in fall with cool temperatures (the plant in the rear left in the photograph is 'Sky Rocket').

Figure 1:
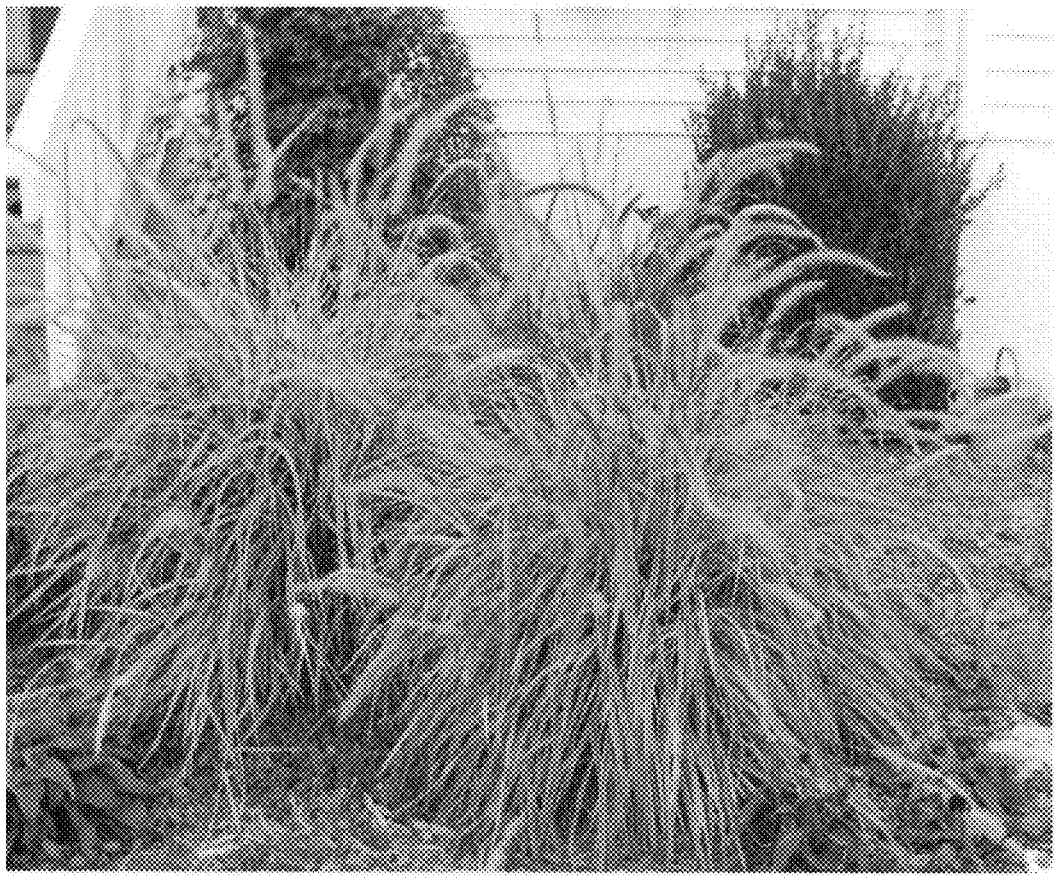
Figure 2:
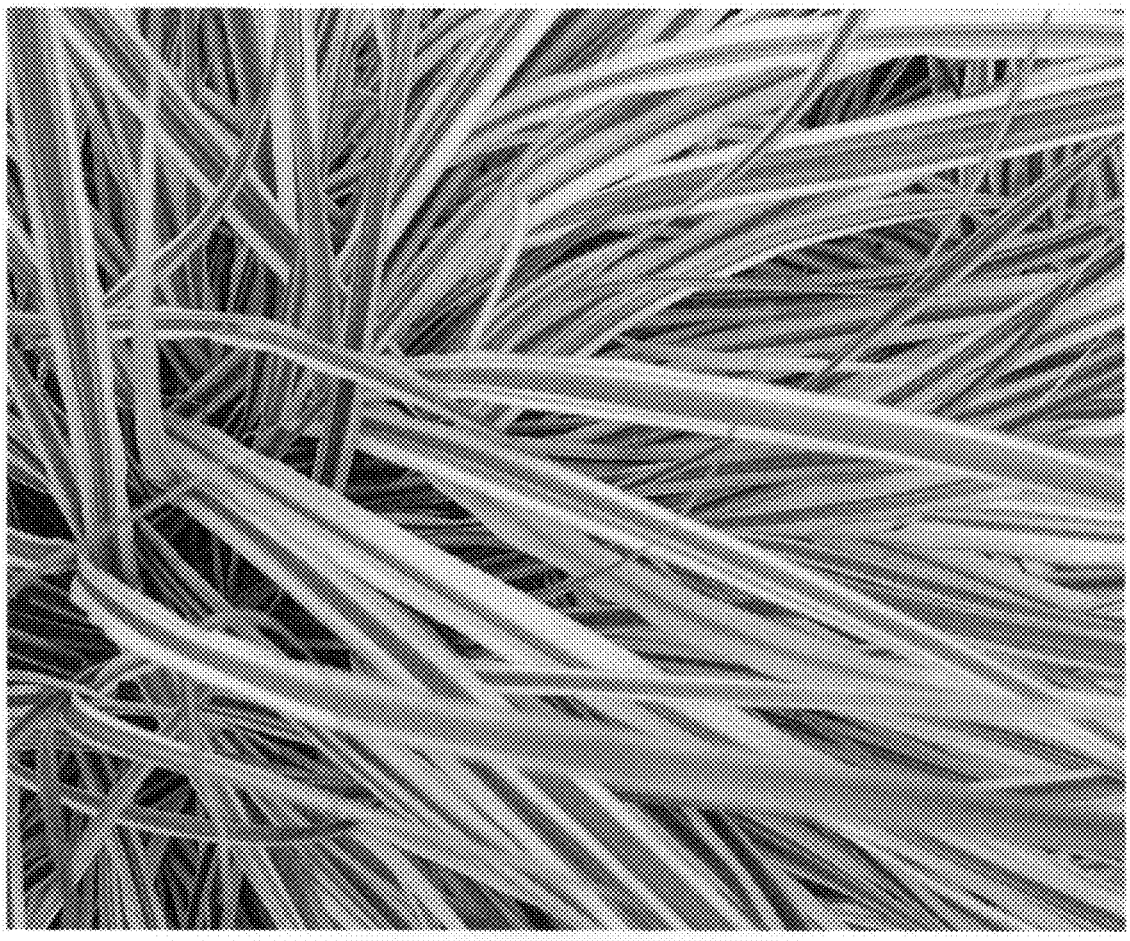

The photograph on FIG. 2 shows a close-up view of the foliage of 'Cherry Sparkler' in spring.

Figure 3:
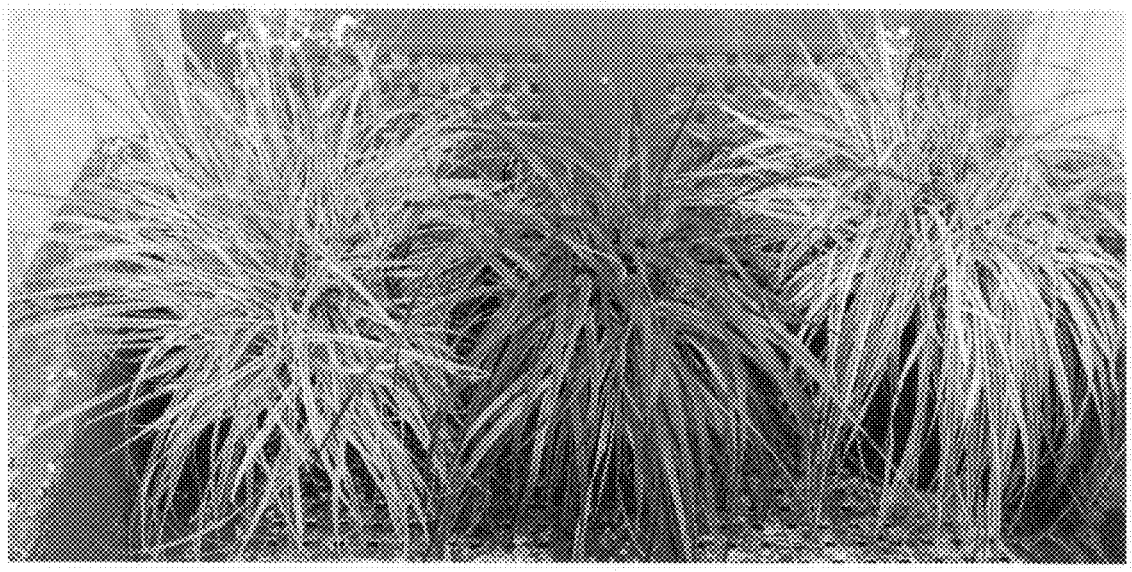

The photograph in FIG. 3 was taken in spring and provides a comparison of plants grown under the same conditions of 'Sky Rocket' (left), 'Fireworks' (center), and 'Cherry Sparkler' (right).

The colors in the photographs are as close as possible with the digital photography and printing techniques utilized and the color codes in the detailed botanical description more accurately describe the new *Pennisetum.*

DETAILED BOTANICAL DESCRIPTION

The general observations and descriptions describe plants about one year in age as grown outdoors in one-gallon containers. The new *Pennisetum* has not been observed under all possible environmental conditions and the phenotype may vary somewhat with variations in temperature, day-length, light intensity, soil types, and water and fertility levels without, however, any variance in genotype. The color determinations are in accordance with he 2007 R.H.S. Colour Chart of The Royal Horticultural Society, London, England, except where general color terms of ordinary dictionary significance are used.

General description:

*Blooming period.*—Blooms from May until frost in Georgia.

*Plant habit.*—Herbaceous, clump-forming, ornamental grass with an upright culms and leaf blades that cascade in a vase-shaped form.

*Height and spread.*—Reaches a height of 91 to 102 cm (36 to 40 inches), and a spread of about 91 cm (36 inches), plants used for data collection grown in one-gallon containers; height 30.5 cm (1 ft) in height and 61 cm (2 ft) in width.

*Cold hardiness.*—U.S.D.A. Zone 10, grown in colder climates as a seasonal grass.

*Culture.*—Grows best in fertile, well-drained soils in full sun, tolerant to wind but performs poorly in wet soils, foliage coloration is best in full sun.

*Diseases and pests.*—No known disease resistance or pest problems.

*Root description.*—Initially fine and becoming fleshy as the plants develop.

Growth and propagation:

*Propagation.*—Culm division.

*Time required for root initiation.*—From a full fan division, roots appear within 10 days in early spring in a propagation house heated to 75° F.

*Time required for root development.*—Roots will fully develop a 72-cell liner in 4 to 5 weeks, and a rooted 72-cell liner will fully develop in a 4-inch container in 6 to 7 weeks.

*Growth rate.*—Vigorous in summer, moderately vigorous in other seasons.

Culm (stem) description:

*General.*—Cylindrical, enclosed by leaf sheaths.

*Culm aspect.*—Held erect to slightly cascading.

*Culm color.*—Ranges from 144B to 144D (comprised of leaf sheaths).

*Culm size.*—An average of 16 cm in length and an average of 5 mm in width.

*Culm surface.*—Glabrous and satiny.

*Internode length.*—Average of 2 cm.

Foliage description:

*Leaf shape.*—Linear.

*Leaf division.*—Simple.

*Leaf base.*—Sheathed.

*Leaf apex.*—Acute, tapering to a fine point.

*Leaf aspect.*—Emerging leaves are erect, leaf blades diverge from leaf sheath at ligule at about a 45° angle from center of culm then gently cascading, blades are flat to slightly concave.

*Leaf venation.*—Parallel, mid rib is recessed on upper surface, color matches the color of the leaf blades on upper and lower surface.

*Leaf margins.*—Entire in appearance but finely scabrous to touch.

*Leaf persistence.*—Foliage dries but is persistent throughout the winter.

*Leaf attachment.*—Sheathed, leaf is sheathed from the base of culm and the blade extends out from the culm at a ligule.

*Ligule.*—Reduced to a row of fine hairs 0.5 mm in length, 144D in color.

*Leaf size.*—Average of 30 cm in length and up to 1.2 cm in width; narrower at culm attachment and tapering to a point at the apex.

*Leaf surface.*—Glabrous on upper and lower surface with satin sheen, but finely scabrous to touch on upper surface.

*Leaf number.*—Average of 6 leaves per culm 18 cm in length.

*Leaf arrangement.*—Alternate, 2 ranked.

*Leaf color and variegation pattern.*—Variegation is comprised of vertical bands of green and creamy white of varying widths (most typically with green centers and creamy white margins) with a flush of pink with sun exposure, variegation pattern and coloration occurs on upper and lower surface, spring leaves; green bands 143C, white bands NN155A becoming flushed with 65A; first at margins and then spreading over the entire leaf blade, mature leaves in sun; green bands a blend of 147A and 143C and creamy white bands 155B in color, pink flush 65A, in fall with cooler temperatures, the amount of flush with 65A becomes more highly expressed.

Flower description:

*General description.*—Inflorescence is a plumed raceme terminating from each culm, arching upward and then cascading, comprised of densely packed spikelets surrounded by an involucre of bristles.

*Lastingness of inflorescence.*—Racemes dry but remain persistent.

*Fragrance.*—None.

*Panicle size.*—An average of 24.5 cm in length and an average of 3 cm in width (including bristles).

*Panicle color.*—Effectively a blend of 161D and 182A due to bristles becoming burgundy color, rachis is about 1 mm in width and 137C in color.

*Spikelet description.*—Single or in groups of 2 to 3, an average of 5 mm (2.2 cm including bristles) and 1.5 mm in width (4 mm including bristles), 2 glumes; membranous, transparent and 155A in color suffused with 182A, 4 mm in length and 1 m in width, palae; about 5 mm in length and 1 mm in length, lemma; translucent and about 155A in color, about 5 mm in length and 1 mm in width, bristles; attached to base of spikelet, up to 3 cm in length, unequal in length, plumose at base, 161C or 187B in color.

*Reproductive organs.*—Pistil; 1 with two plumose stigmas about 7 mm in length, 0.5 mm in width and 155A in color, stamens; 2, shorter that stigmas, 1.8 mm in length, 0.5 mm in width and 152C in color, pollen; not visible, seed; seed set was not observed.

The invention claimed is:

1. A new and distinct cultivar of *Pennisetum* plant named 'Cherry Sparkler' as herein illustrated and described.

* * * * *